US005545139A

United States Patent [19]

Kriesel

[11] Patent Number: 5,545,139
[45] Date of Patent: * Aug. 13, 1996

[54] FLUID CONTAINER FOR USE WITH A FLUID DELIVERY APPARATUS

[75] Inventor: Marshall S. Kriesel, St. Paul, Minn.

[73] Assignee: Science Incorporated, Bloomington, Minn.

[ * ] Notice: The portion of the term of this patent subsequent to Sep. 29, 2013, has been disclaimed.

[21] Appl. No.: 349,404

[22] Filed: Dec. 2, 1994

Related U.S. Application Data

[63] Continuation of Ser. No. 129,470, Sep. 29, 1993, Pat. No. 5,374,256, which is a continuation-in-part of Ser. No. 129,693, Sep. 29, 1993, Pat. No. 5,419,771, which is a continuation-in-part of Ser. No. 69,937, May 28, 1993, Pat. No. 5,336,188, which is a continuation-in-part of Ser. No. 46,438, May 18, 1993, Pat. No. 5,411,480, which is a continuation-in-part of Ser. No. 987,021, Dec. 7, 1992, Pat. No. 5,279,558, which is a continuation of Ser. No. 870,269, Apr. 17, 1992, Pat. No. 5,205,820, which is a continuation-in-part of Ser. No. 642,208, Jan. 16, 1991, Pat. No. 5,169,389, which is a continuation-in-part of Ser. No. 367,304, Jun. 16, 1989, Pat. No. 5,019,047.

[51] Int. Cl.$^6$ .................................................. A61M 37/00
[52] U.S. Cl. ........................ 604/132; 604/890.1; 604/232; 604/189; 128/DIG. 12
[58] Field of Search ........................... 604/83, 87, 89, 604/187, 189, 190, 201, 203, 232–236, 131, 132, 151, 153, 246; 128/DIG. 12

[56] References Cited

U.S. PATENT DOCUMENTS

| | | | |
|---|---|---|---|
| 4,048,997 | 9/1977 | Raghavachari et al. | 604/189 |
| 4,474,575 | 10/1984 | Eckenhoff et al. | 604/131 |
| 4,968,301 | 11/1990 | di Palma et al. | 604/132 |
| 5,122,116 | 6/1992 | Kriesel et al. | 604/89 |
| 5,176,641 | 1/1993 | Idriss | 604/133 |
| 5,248,300 | 9/1993 | Bryant et al. | 604/134 |
| 5,267,957 | 12/1993 | Kriesel et al. | 604/85 |
| 5,328,464 | 7/1994 | Kriesel et al. | 604/83 |
| 5,330,426 | 7/1994 | Kriesel et al. | 604/89 |
| 5,336,180 | 8/1994 | Kriesel et al. | 604/82 |

Primary Examiner—Corrine M. McDermott
Attorney, Agent, or Firm—J. E. Brunton

[57] ABSTRACT

A fluid container assembly which can be aseptically filled in the field with selected fluids and one which is specially designed for sterile coupling and use with fluid dispensing and delivery devices of the character that embody stored energy sources such as compressible cellular masses and distendable elastomeric membranes that form, in conjunction with a cooperating base, fluid chambers for containing the fluid to be dispensed.

15 Claims, 2 Drawing Sheets

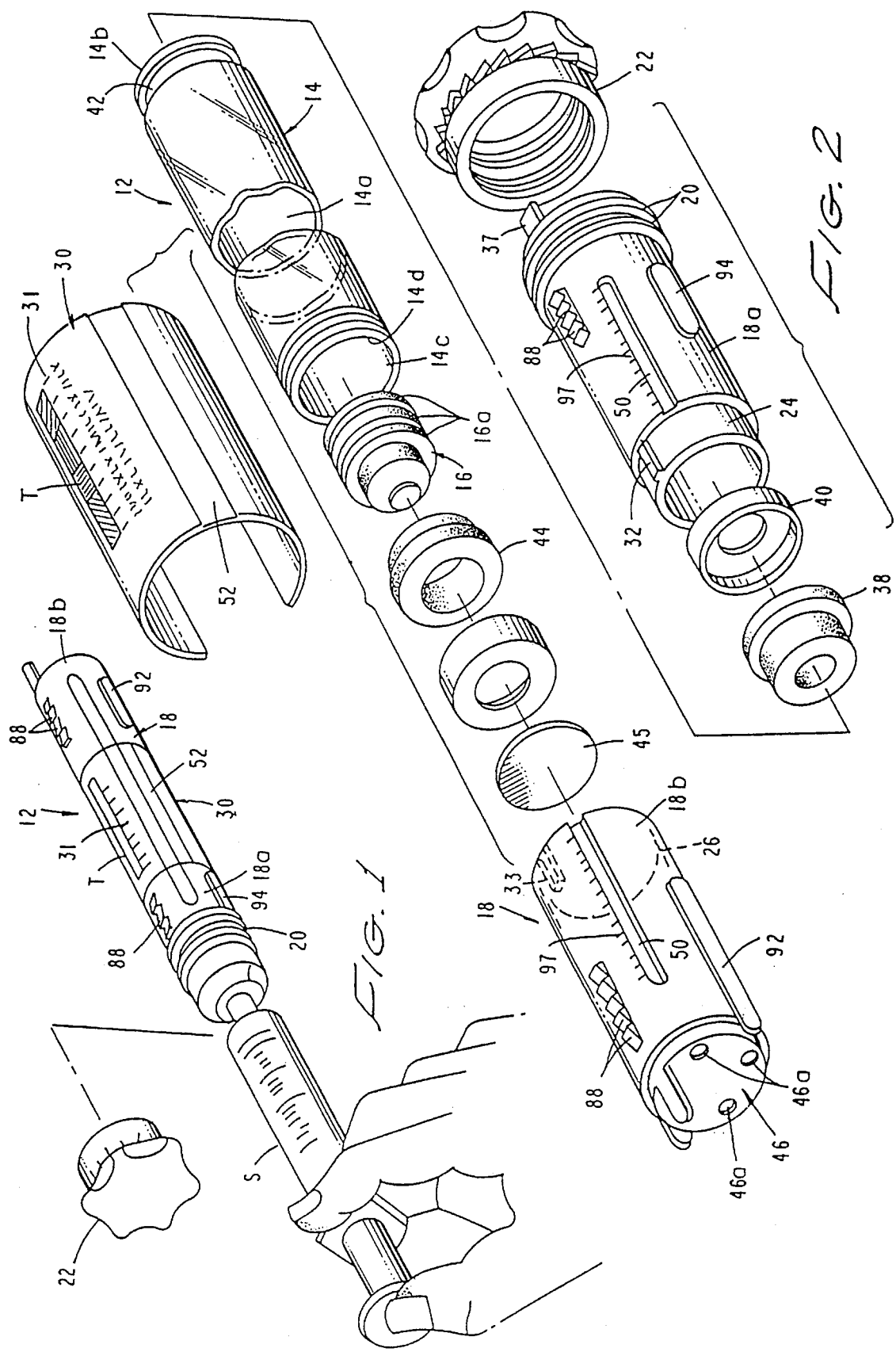

FLUID CONTAINER FOR USE WITH A FLUID DELIVERY APPARATUS

This is a Continuation of application Ser. No. 08/129,470 filed Sep. 29, 1993, now U.S. Pat. No. 5,374,256, which is a Continuation In Part of application Ser. No. 08/129,693 filed Sep. 29, 1993, now U.S. Pat. No. 5,419,771, which is a Continuation In Part of application Ser. No. 08/069,937 filed May 28, 1993 which has issued into U.S. Pat. No. 5,336,188, which is a Continuation In Part of application Ser. No. 08/046,438 filed May 18, 1993, now U.S. Pat. No. 5,411,480, which is a Continuation In Part of application Ser. No. 07/987,021 filed Dec. 7, 1992 and which has issued into U.S. Pat. No. 5,279,558, which is a Continuation of application Ser. No. 07/870,269 filed Apr. 17, 1992 which has now issued into U.S. Pat. No. 5,205,820 and which is, in turn, a Continuation In Part of application Ser. No. 07/642,208 filed Jan. 16, 1991, which has now issued to U.S. Pat. No. 5,169,389 which is a Continuation In Part of application Ser. No. 07/367,304 filed Jun. 16, 1989 which has now issued to U.S. Pat. No. 5,019,047.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time and to a novel fluid containing vial assembly which can be field filled and then used to charge the fluid reservoirs of the fluid delivery apparatus.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films, expandable foams and similar materials, which, in cooperation with a base defines a fluid chamber that contains the fluid which is to be dispensed. The elastomeric film membrane or the expandable foam member controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending USSN 08/046,438 filed by the present inventor on Apr. 13, 1993 also describes various types of expandable cellular elastomers and elastomeric foams used in making the expandable member of various physical embodiments of the invention. This co-pending application is also hereby incorporated by reference in its entirety as though fully set forth herein.

The apparatus of the invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the devices described in Continuation-In-Part U.S. Pat. No. 5,336,188 and illustrated in FIGS. 34 and 35 thereof includes first, second, and third cooperating fluid chambers which can be selectively filled by individual fluid containers or vials containing various fluids such as diluents and medicaments. The novel apparatus shown in FIGS. 34 and 35 permits two or more liquid components to be stored within the reservoirs of the apparatus and then controllably intermixed at the time of fluid delivery. In an application filed concurrently with the present application there is described a number of inventions which expand on inventions described in the 5,336,188 patent by providing a novel platform support system to which several fluid dispensers of varying volume can be operably interconnected. Both this last mentioned application filed on even date herewith and U.S. Pat. No. 5,336,188 are incorporated herein by reference as though fully set forth herein.

The present application expands further on the concepts disclosed in the applications identified in the preceding paragraph by providing a novel fluid container or vial that is usable with the apparatus of these inventions and is of a unique design which permits it to be expeditiously filled in the field.

SUMMARY OF THE INVENTION

It is an object of the present invention to provide an apparatus for expelling fluids at a precisely controlled rate which is of a compact, low profile, laminate construction. More specifically, it is an object of the invention to provide such an apparatus which can be used for the precise infusion of pharmaceutical fluids to an ambulatory patient at controlled rates over extended periods of time.

It is a particular object of the invention to provide a device of the aforementioned character which embodies stored energy sources such as distendable elastomeric membranes, that form in conjunction with a cooperating base, fluid chambers for containing the fluids to be dispensed. The novel aseptically field fillable vial assembly of the present invention is specially designed for use with these types of devices so that they can be expeditiously filled in the field shortly before use with a wide variety of medicinal fluids.

By way of summary description, the novel vial construction of the present invention permits field filling of either individual fluid dispensers of the character described in the preceding paragraphs, or alternatively, permits the field filling of multireservoir devices which allow for the controlled delivery therefrom of large volumes of the same or different fluids at controlled rates in accordance with a predetermined delivery protocol.

In one form of the fluid container of the present invention, the fluid chamber thereof can also be quickly and easily filled in the field using a conventional hypodermic syringe. After filling, the vial assembly can be coupled with the delivery system in a manner to insure the aseptic transfer of the fluid to be delivered.

Another object of the invention is to provide field fillable vial assemblies of the class described which can be filled and then stored under refrigeration for an extended period. For those types of assemblies, a novel temperature indicator is provided as an integral part of the assembly.

Other objects of the invention are set forth in U.S. Pat. No. 5,205,820 and Ser. No. 08/069,937 which are incorporated herein and will become more apparent from the discussion which follows.

BRIEF DESCRIPTION OF THE DRAWINGS

FIG. 1 is a generally perspective, exploded view of one form of the field filled vial assembly of the present invention showing it being filled by means of a conventional hypodermic syringe.

FIG. 2 is an exploded, generally perspective view of one form of the fluid container or vial assembly of the invention.

DESCRIPTION OF THE INVENTION

Figure 3:
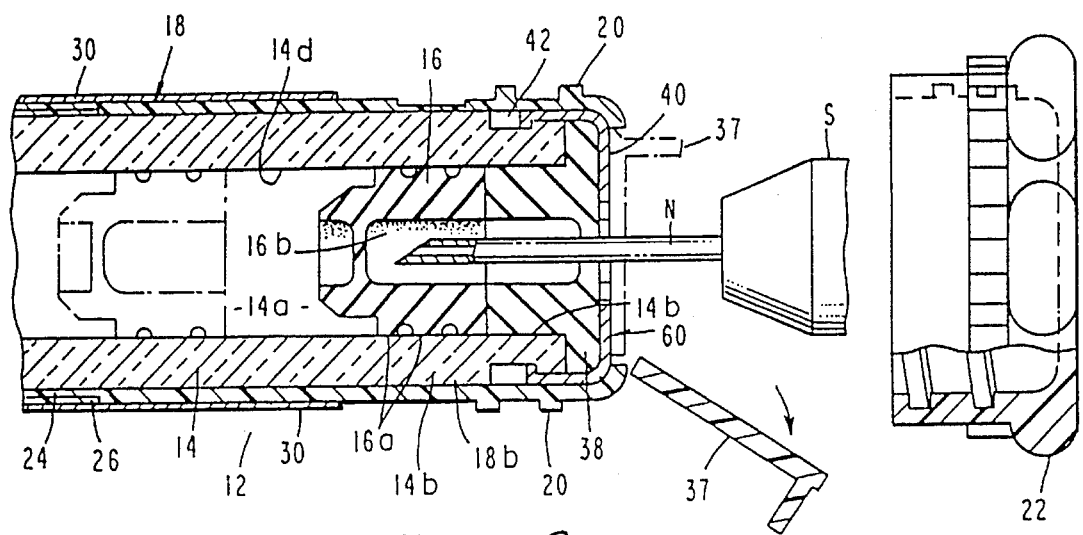
FIG. 3 is an enlarged, fragmentary, cross-sectional side view of the vial assembly showing the cap removed and the internal plunger thereof being pierced by the syringe needle.

Referring to the drawings and particularly to FIGS. 1 through 3, one form of the vial assembly of the invention is there illustrated and generally identified by the numeral 12. The apparatus comprises a transparent container, or vial, 14 having a fluid chamber 14a for containing the fluid to be added to the reservoir of a fluid dispenser or other fluid delivery device. The fluid can be a diluent or any of the medicaments or beneficial agents described in the previously identified U.S. Pat. No. 5,205,820. Vial 14 has open ends 14b and 14c and closely receives a piercable piston-like plunger 16 which is movable within vial 14 from a first position, shown in FIG. 3, where it is proximate end 14b of the vial to a second position where it is disposed proximate end 14c of the vial. Container 14 can be a glass vial or any other suitable sterile container for containing the fluid that is to be used in filling the reservoirs of the fluid dispensers or fluid delivery devices.

Also forming a part of the vial assembly of the present embodiment of the invention is an outer safety casing 18, shown here as comprising cooperating first and second portions 18a and 18b which are joined to form a sterile barrier system. First portion 18a is provided with threads 20 and is closed by a threaded closure cap 22. Provided at its open end is a socket like construction 24 which is telescopically received within the open end portion 26 of second casing portion 18b. Outer casing 18 is receivable over vial 14 and portions 18a and 18b are held in mating engagement by an overwrap 30 which functions as an interface sterility barrier and upon which appropriate identifying indicia 32 can be imprinted. A novel temperature indicator means, such as indicator "T" is also carried by overwrap 30 Indicator "T" may be a reversible liquid crystal temperature bar indicator of a character which is readily commercially available from sources such as Clark Research and Development of Chicago, Ill., Thermax of Anaheim, Calif. and American Thermo Instruments of Dayton, Ohio. Indicator "T" provides information as to the approximate temperature of the vial assembly during storage and at time of use. As shown in FIG. 2, a guide bead 32 is provided on portion 24. Bead 32 is receivable within a corresponding channel 34 provided in portion 18b to insure that portions 18a and 18b of the outer casing are properly aligned.

In a manner presently to be described, as the fluid chamber of the vial is filled with fluid using syringe "S" (FIG. 1), penetrable piston 16 is moved within the vial from the first position shown in FIG. 3 to a second position wherein it is disposed proximate end 14c. Piston 16 is provided with a plurality of circumferentially extending sealing beads 16a which sealably engage the inner walls 14d of container 14 as the piston moves rearwardly thereof so as to prevent fluid leakage past the piston.

Referring now to FIG. 3, after the vial assembly has been assembled in the manner shown in FIG. 1 and with cap 22 removed, a tear away closure cover 37 is removed. Next the needle "N" of the syringe "S" is used to penetrate a piercable means shown here as an elastomeric plug 38 which closes end 14b of vial 14. As shown in FIG. 3, plug 38 is held in position within vial 14 by an aluminum crimp cap 40, the periphery of which is crimped over into a circumferential groove 42 provided proximate end 14b of the vial. As fluid is forced from the syringe into an interior chamber 16b of plunger 16, the plunger will be forced to the left until it moves into close proximity with end 14c of the vial where it engages a retainer ring 44 (FIG. 2) that is closely received within end 14c of the vial. During the vial filling step, air disposed within chamber 14c will be expelled through a sterile vent patch 45 which is bonded to a closure cap 46 that is provided with vent apertures 46a.

After the vial has been filled with the selected fluid, cap 22 is reconnected with the outer casing 18 so as to maintain the interior of the vial in a sealed, aseptic condition. As best seen in FIG. 2, casing 18 is provided with an elongated viewing slot 50 that permits viewing of the interior chamber 14c of the vial. Similarly, overwrap 30 has an elongated viewing slot 52 which is indexable with slot 50. With this construction, the user can tell at a glance whether the vial is full or empty.

In its sealed, aseptic condition with a sterile fluid path, vial assembly 12 can be stored as may be necessary until it is to be used to fill a fluid dispenser or a reservoir of a delivery apparatus such as that shown in FIGS. 34 and 35 of U.S. Pat. No. 5,336,188.

Figure 4:
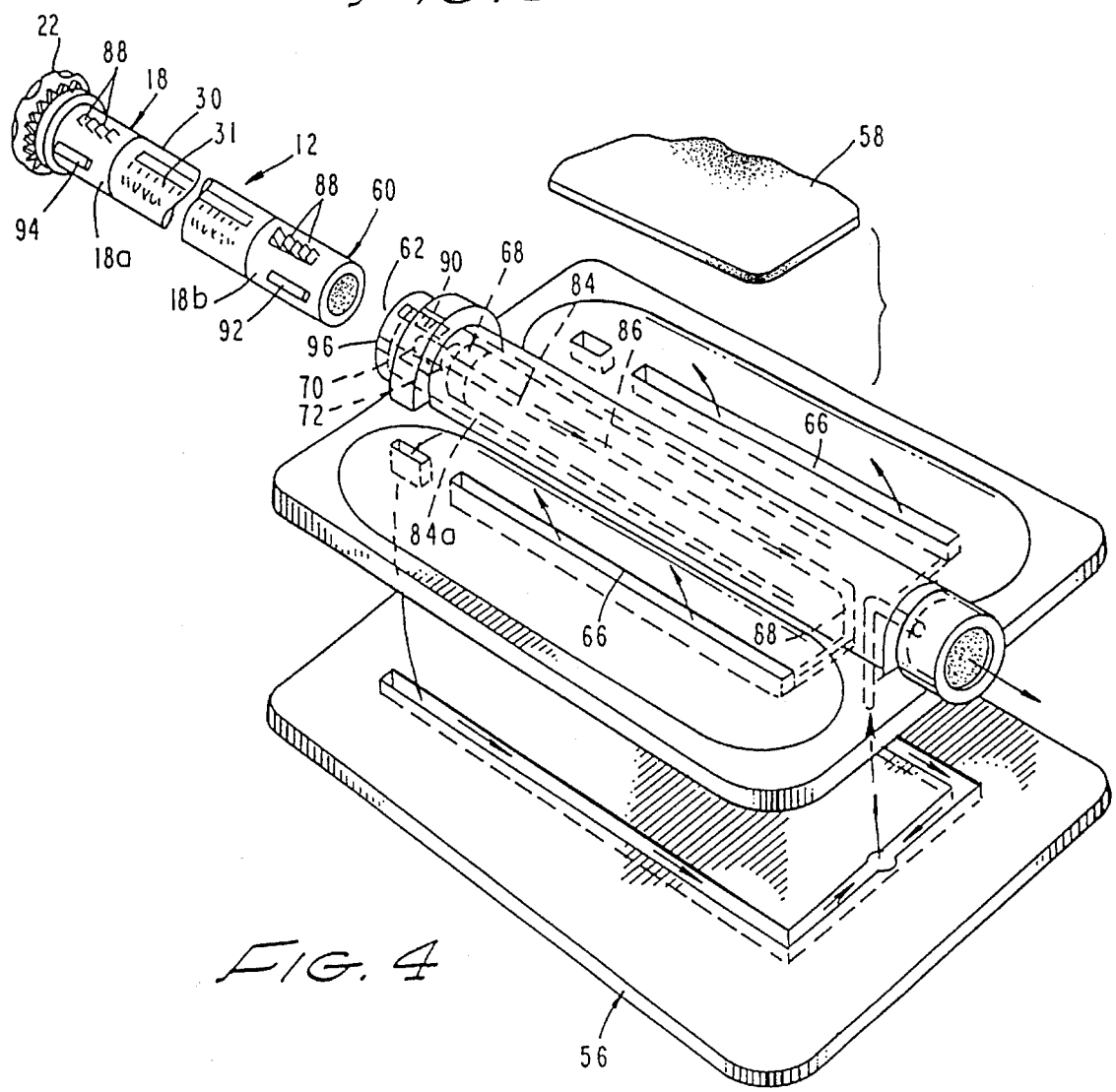
FIG. 4 is a fragmentary, perspective view of one form of the fluid dispenser with which the vial assembly of the present invention can be used.

Turning now to FIG. 4, the vial assembly is there shown being used to fill the fluid chamber of a fluid dispenser of the character having a base 56, a stored energy means for forming, in conjunction with the base, a fluid chamber and a cover means which is receivable over the base for sealably enclosing the stored energy means. The stored energy means is here shown as comprising a distendable membrane 58, of the general character described in U.S. Pat. No. 5,205,820 at Column 9, Lines 3–59. The cover means here comprises a cover 34 of the general character shown in FIG. 41 of U.S. Pat. No. 5,205,820 (see FIG. 41 of U.S. Pat. No. 5,205,820 which is incorporated herein by reference).

After tear-away cover 46 has been removed from the vial assembly (FIG. 2), the outboard end 60 of the vial assembly, which presents a sterile interface, is inserted into the likewise sterile inlet opening 62 of the dispenser unit to accomplish a sterile coupling. As indicated in FIG. 4, the dispenser unit is provided with first flow means for establishing sterile fluid communication between the fluid inlet 66 of the reservoirs of the fluid dispenser and chamber 14c of vial 14, when the filling assemblage is mated with the fluid dispenser. In the embodiment of the invention, shown in FIG. 4, the first flow means comprises a piercing cannula assembly 68 which includes an outwardly protruding hollow cannula 70. The cannula assembly 68 also includes a housing 72 which supports hollow cannula 70. Housing 72 is connected to the outboard end 84a of an elongated stem 84 which is provided with a central fluid passageway 86 that communicates with the reservoirs of the fluid dispenser.

After end 60 of the vial assembly is inserted into inlet port 62 of the fluid dispenser, an inward pressure exerted against the vial assembly will cause hollow cannula 70 to penetrate penetrable piston 16 of the vial assembly opening a fluid flow passageway between passageway 86 of the fluid dispenser and chamber 14c of the vial assembly. As shown in FIG. 4, casing 18b of the vial subassembly is provided with a multiplicity of outwardly extending, resiliently deformable locking elements 88, which comprise a part of the interlocking means of the invention for interlocking together the vial assembly and the fluid dispenser. Elements 88 are adapted to slide past a multiplicity of inwardly extending teeth 90 provided within inlet 62 of the fluid dispenser. These teeth are so constructed and arranged as to engage elements 88 in a manner to permit insertion of the vial assembly into the dispenser inlet but to prevent its removal after it has been fully telescopically inserted into the inlet of the fluid dispenser. To insure proper alignment between the filling subassembly and the inlet of the fluid dispenser, forward and rearward guide rails 92 and 94 are closely receivable within longitudinally extending tracks 96 provided within the inlet of the fluid dispenser. The coupling of the vial assembly with the fluid dispenser is more fully described in the application filed concurrently herewith.

As previously mentioned, indicator means are provided for indicating the volume of fluid remaining within vial 14 as the vial assembly is inserted into the inlet of the fluid dispenser. This indicator means comprises the previously identified viewing slots 50 and 52 along which are disposed a multiplicity of indicating indicia 97. Since vial 14 is transparent, the amount of fluid remaining within the vial at any point in time can readily be determined by merely aligning one of the indicia markings on the casing with the inboard extremity of piston 16 as it moves toward its innermost position.

As previously mentioned, the vial assemblies of the present invention can also be conveniently coupled with connector means 414a, 414b and 414c of the multireservoir devices illustrated in FIGS. 34 and 35 of U.S. Pat. No. 5,336,188 and can be used to fill the reservoirs of these devices in the manner described in this co-pending application.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for use in infusing fluids into an ambulatory patient at a controlled rate comprising:

(a) a base having a fluid inlet and fluid outlet interconnected by a fluid flow path;

(b) filling means operably associated with said base for introducing fluid into said fluid inlet of said base, said filling means comprising:

(i) a container having a fluid chamber with first and second open ends;

(ii) piercable means for sealably closing one of said first and second open ends of said container, said piercable means being piercable by a cannula; and (iii) a plunger telescopically movable within said container by fluid pressure from a first location proximate said piercable means to a second, spaced-apart location; and (c) a distendable membrane constructed of an elastic material which is fitted over said base to define a chamber in communication with said fluid inlet and said fluid outlet of said base, said membrane being distendable by fluid introduced into said chamber under pressure through said fluid inlet by said filling means, said membrane having a tendency to return to a substantially nondistended configuration whereby fluid within said chamber will be expelled through said fluid outlet.

2. An apparatus as defined in claim 1 in which said plunger is piercable by a cannula.

3. An apparatus as defined in claim 2 in which said device further includes interconnecting means for interconnecting said fluid chamber of said container with said inlet of said base, said interconnecting means comprising a cannula having a first end adapted to penetrate said piercable plunger when said plunger is in said second location and a second end in communication with said chamber defined by said membrane and said base.

4. An apparatus as defined in claim 3 in which said filling means further includes an outer casing surrounding said container, said casing having first and second ends.

5. An apparatus as defined in claim 4 in which one of said first and second ends of said casing is closed by a removable closure cap and the other of said first and second ends of said casing is closed by closure assembly having vent means for venting said fluid chamber.

6. An apparatus as defined in claim 5 in which said casing is provided with indicator means for indicating the volume of fluid within said chamber of said container.

7. An apparatus as defined in claim 6 in which said indicator means comprises an elongated viewing slot formed in said casing and indicating indicia marked on said casing proximate said slot.

8. An apparatus as defined in claim 7 further including temperature indicating means provided on said casing for indicating the temperature of the apparatus.

9. A device for use in infusing fluids into an ambulatory patient at a controlled rate comprising:
 (a) a base having an inlet opening defining a fluid inlet, said base also having a fluid outlet interconnected with said fluid inlet by a fluid flow path;
 (b) filling means for introducing fluid into said fluid inlet, said filling means comprising:
  (i) a container receivable within said inlet opening, said container having a fluid chamber with first and second open ends;
  (ii) piercable means for sealably closing one of said first and second open ends of said container, said piercable means being piercable by a piercing cannula; and
  (iii) a plunger telescopically movable within said container by fluid pressure from a first location proximate said piercable means to a second, spaced-apart location; and
 (c) a distendable membrane constructed of an elastic material which is fitted over said base to define a chamber in communication with said fluid inlet and said fluid outlet, said membrane being distendable by fluid introduced into said chamber under pressure through said fluid inlet, said membrane having a tendency to return to a substantially nondistended configuration whereby fluid within said chamber will be expelled through said fluid outlet.

10. A device as defined in claim 9 further including indicator means carried by said filling means for indicating the volume of fluid within said chamber of said container.

11. A device as defined in claim 9 further including temperature indicating means carried by said filing means for indicating the temperature of the device.

12. A vial assembly for containing an infusible liquid, said vial assembly comprising:
 (a) a container having a liquid chamber with first and second open ends;
 (b) piercable means for sealably closing one of said first and second open ends of said container, said piercable means being piercable by a piercing cannula;
 (c) a plunger telescopically movable within said container by liquid pressure from a first location proximate said piercable means to a second, spaced-apart location; and
 (d) an outer casing surrounding said container said casing having first and second ends, one of said first and second ends being closed by a closure cap and the other of said first and second ends being closed by a closure assembly comprising vent means for venting said chamber to atmosphere.

13. A vial assembly as defined in claim 12 in which said venting means comprises a vent patch.

14. A vial assembly as defined in claim 12 in said container is transparent and in which said casing is provided with indicator means for indicating the volume of fluid within said chamber of said container and with temperature indicating means for indicating the temperature of the vial assembly.

15. A vial assembly as defined in claim 14 in which said indicator means comprises an elongated viewing window formed in said casing and indicating indicia marked on said casing proximate said window.

* * * * *